(12) United States Patent
Sommer

(10) Patent No.: US 6,871,085 B2
(45) Date of Patent: Mar. 22, 2005

(54) CARDIAC VEIN LEAD AND GUIDE CATHETER

(75) Inventor: John L. Sommer, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 22 days.

(21) Appl. No.: 10/261,315

(22) Filed: Sep. 30, 2002

(65) Prior Publication Data

US 2004/0064024 A1 Apr. 1, 2004

(51) Int. Cl.⁷ .............................. A61B 5/04; A61N 1/05
(52) U.S. Cl. ......................... 600/374; 600/381; 606/41; 607/122
(58) Field of Search ............................... 600/374, 381, 600/585; 606/41; 607/122

(56) References Cited

U.S. PATENT DOCUMENTS

| | | | |
|---|---|---|---|
| 4,664,120 A | * 5/1987 | Hess ........................... | 600/374 |
| 5,396,902 A | 3/1995 | Brennen et al. ............ | 128/772 |
| 5,531,685 A | 7/1996 | Hemmer et al. ............. | 604/95 |
| 5,807,249 A | 9/1998 | Qin et al. .................... | 600/374 |
| 5,895,416 A | 4/1999 | Barreras et al. | |
| 5,935,160 A | 8/1999 | Auricchio et al. .......... | 607/122 |
| 6,030,405 A | 2/2000 | Zarbatany et al. .......... | 606/191 |
| 6,217,576 B1 | 4/2001 | Tu et al. | |
| 6,322,534 B1 | 11/2001 | Shkolnik ................. | 604/96.01 |
| 6,366,819 B1 | 4/2002 | Stokes ......................... | 607/119 |
| 2001/0039413 A1 | * 11/2001 | Bowe ......................... | 607/122 |
| 2002/0072737 A1 | 6/2002 | Belden et al. | |

FOREIGN PATENT DOCUMENTS

| | | |
|---|---|---|
| EP | 0790066 B1 | 4/2000 |
| WO | WO 02/22196 A1 | 3/2002 |

* cited by examiner

Primary Examiner—Lee S. Cohen
(74) Attorney, Agent, or Firm—Girma Wolde-Michael; Michael C. Soldner

(57) ABSTRACT

A guide catheter and medical lead are provided wherein the lead may be used as a pull wire to steer the guide catheter. The guide catheter is provided with a flexible distal segment and the lead is provided with a distal engaging member, which may also serve as an electrode. The distal engaging member interacts with the distal catheter end such that traction applied to the proximal lead end causes flexion of the distal segment of the catheter to advance the flexible distal segment between a non-flexed position and a flexed position, allowing the catheter to be steered around obstacles.

7 Claims, 10 Drawing Sheets

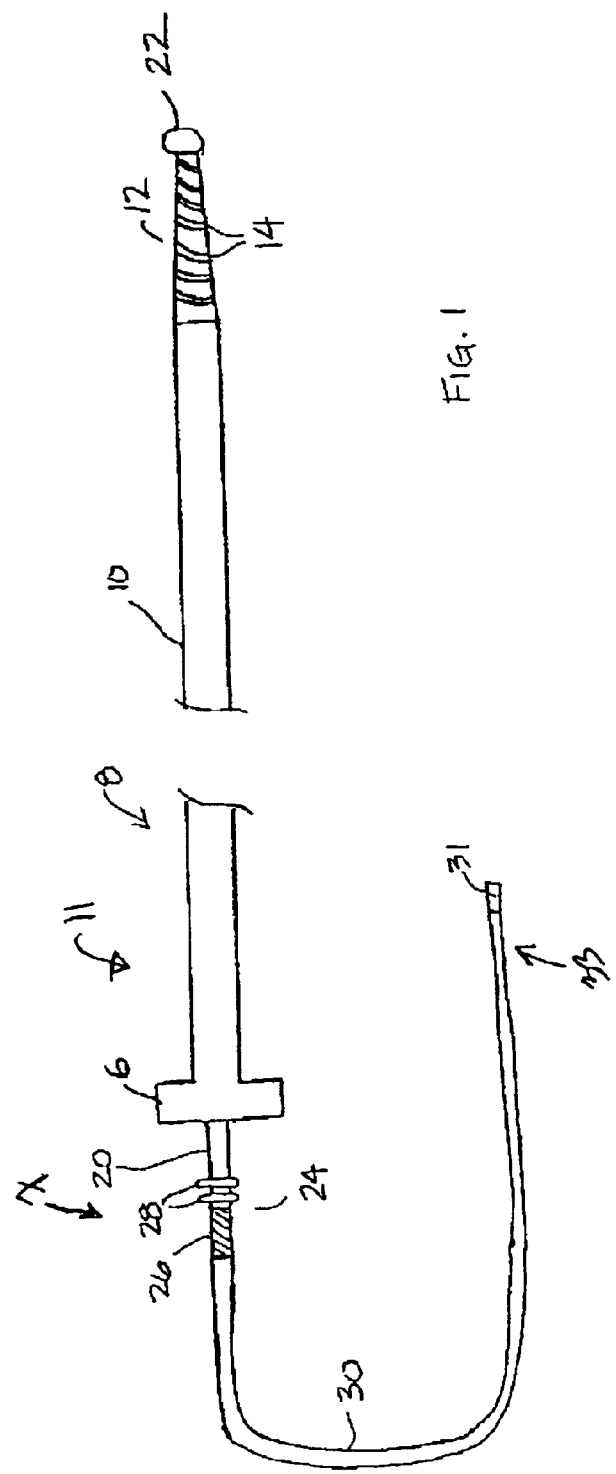

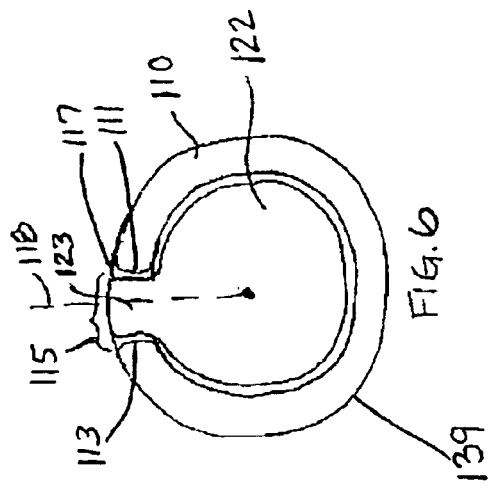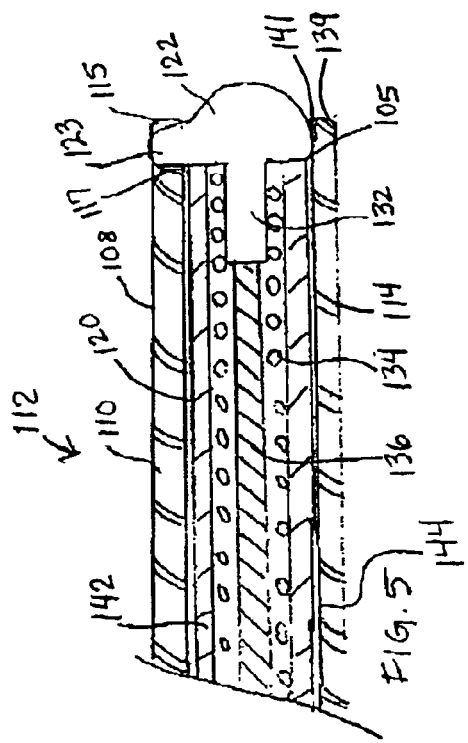

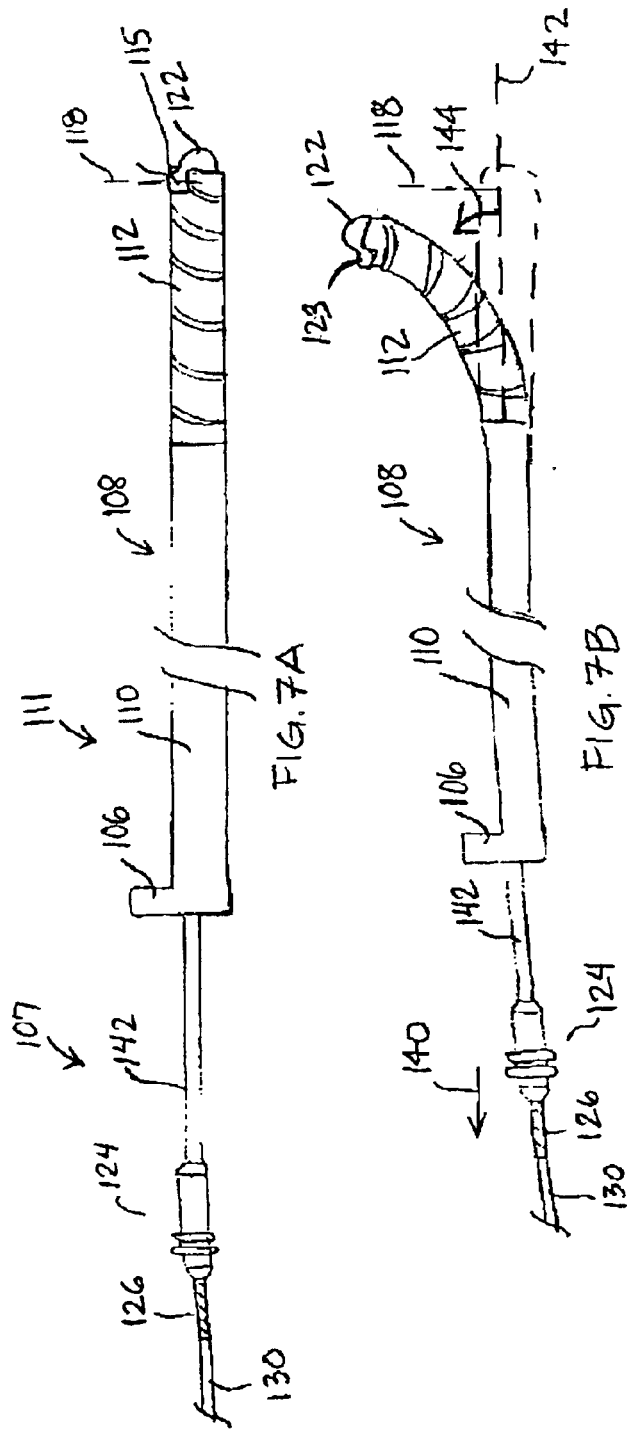

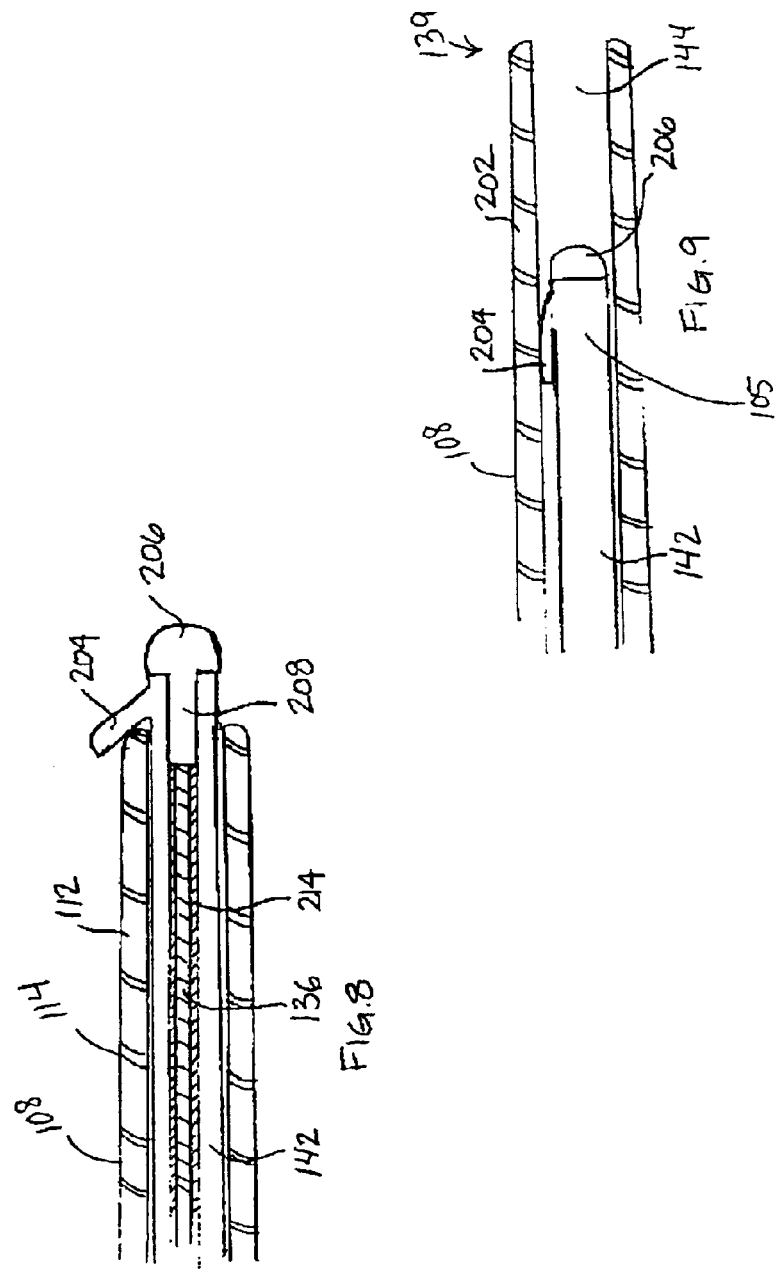

US 6,871,085 B2

CARDIAC VEIN LEAD AND GUIDE CATHETER

FIELD OF THE INVENTION

The present invention generally relates to implantable medical device catheters and implantable medical device leads, and more particularly, the present invention relates to a guide catheter for use in implanting a medical lead wherein the guide catheter may be steered to a desired location in a patient's body using a high tensile strength medical lead as a pull wire.

BACKGROUND OF THE INVENTION

Transvenous endocardial leads may be placed inside a chamber of a patient's heart by passing the lead through a venous entry site, such as the subclavian vein or the cephalic vein, or a tributary thereof, along a venous pathway into the superior vena cava and into the right cardiac chambers. Cardiac vein leads may be advanced further, from the right atrium through the coronary sinus ostium into the coronary sinus and ultimately into one of the various cardiac veins for stimulation and/or sensing of the left heart chambers.

Cardiac lead placement is important in achieving proper stimulation or accurate sensing at a desired cardiac location. Endocardial or cardiac vein leads are generally implanted with the use of a guide catheter or a guidewire or stylet to achieve proper placement of the lead. Cardiac leads generally need to be highly flexible in order to withstand flexing motion caused the beating heart without fracturing. A stiff guidewire or stylet provides a flexible lead with the stiffness needed to advance the lead through a venous pathway. During an implantation procedure, the stylet or guidewire may be removed and replaced by a stylet or guidewire having a different curvature at its distal end to allow the physician to steer the lead through variable curves and branches encountered along a venous pathway. Repeated withdrawal and reinsertion of a stylet or guidewire, however, can be time consuming, increase the risk of infection, and increase the risk of damaging the lead or a blood vessel. Multiple stylets or guidewires having differently sized curvatures at the distal end may be required during a single implant procedure, increasing the number of steps and time involved in implanting a lead.

Guide catheters may also be used to guide the implantation of a medical lead, or various other medical devices, such as angioplasty balloon catheters, ablation catheters, electrophysiological diagnostic catheters, or other devices. Some catheters, particularly electrophysiological diagnostic catheters, may be provided with steering mechanisms that allow the distal end of the catheter to be bent or curved in a desired direction to overcome an obstacle. One mechanism for controlling the curvature or bend applied to the distal end of a catheter includes the use a pull wire. A pull wire is generally attached to a point at the distal end of the catheter such that when traction is applied to the pull wire, the distal end of the catheter is caused to curve or bend. A steerable stylet and manipulative handle assembly, which includes a traction element or pull wire, for guiding a lead or a catheter to a desired location is disclosed in U.S. Pat. No. 5,396,902 issued to Brennen, et al. An electrophysiology catheter assembly which uses a single core wire to cause the tip section of the catheter to deflect is disclosed in U.S. Pat. No. 5,807,249 issued to Qin, et al.

A guide catheter is generally required to possess a certain amount of stiffness to allow the guide catheter to be advanced through body vessels or cavities, yet the guide catheter must be flexible enough to maneuver around obstacles or through a tortuous pathway. Compromise between these design requirements may be met by providing guide catheters having variable stiffness along their length. Greater flexibility near the distal end of a catheter allows the distal end to be more easily maneuvered. A variable stiffness balloon catheter is disclosed in U.S. Pat. No. 6,322,534, issued to Shkolnik, wherein a relatively stiff shaft portion is reinforced with a braided layer and a more flexible distal portion is reinforced with a single helical wire coil. A dilation catheter with a stiffening wire having at least two stepped diameter reductions along its length to vary stiffness from a stiff proximal end to a less stiff distal end is disclosed in U.S. Pat. No. 6,030,405 issued to Zarbatany et al. Variation in stiffness and curvature of a guide catheter tip section may also be accomplished using a temperature-activated memory material such as nitinol. Shape memory elements for controlling steering and/or stiffness of medical devices, such as guide catheters, are disclosed in U.S. Pat. No. 5,531,685 issued to Hemmer et al.

In one prior art method for implanting a cardiac vein lead, a steerable electrophysiology diagnostic catheter is advanced through a guide catheter and used to steer the guide catheter into the coronary sinus. The diagnostic catheter is then removed from the guide catheter and a lead is advanced through the guide catheter into the coronary sinus. Because the size of the guide catheter that can accommodate a steerable diagnostic catheter is generally too large to be advanced further into the deeper coronary veins, a stylet or guidewire is inserted through a lumen of the lead to provide the lead with stiffness needed to advance the lead through the cardiac veins. This procedure involves the use of several different instruments, requires considerable skill, and is generally time-consuming.

In regard to cardiac lead applications, therefore, it is desirable to provide a guide catheter and medical lead system that may be of a reduced size to allow advancement into narrow blood vessels, in particular into the cardiac veins. A cardiac vein lead having a reduced outer diameter that may include a flexible tip is disclosed in U.S. Pat. No. 5,935,160 issued to Auricchio et al. The methods for implanting the cardiac vein lead, however, may still require the use of a guide catheter and/or a guidewire or stylet and the additional steps associated with placing and removing a guidewire or stylet. It is desirable, therefore, to provide a system for dynamically steering a small diameter guide catheter and lead to a desired location without the need for guidewires or stylets, thereby simplifying the implantation procedure and reducing the procedure time.

SUMMARY OF THE INVENTION

The present invention addresses these needs by providing a guide catheter that is easily steered through a vascular pathway for implantation of a medical lead without the use of an additional guidewire or stylet. By eliminating the need for a guidewire or stylet, the overall lead and guide catheter size can be reduced. Moreover, the present invention allows the guide catheter to be dynamically steered without incorporating additional components such as a pull wire in the guide catheter.

The present invention is realized by providing a guide catheter having a flexible distal segment and a medical lead having a high tensile strength and distal engaging member designed to interface with the distal catheter end such that the lead may be used in place of a pull wire for steering the guide catheter. The guide catheter includes a tubular body with a proximal handle and a flexible distal segment. The lumen of the catheter body is sized to allow easy passage of the medical lead. The distal segment, which may be tapered, is sized to form a slip fit with the distal end of the medical lead. The medical lead is fed into the guide catheter by inserting the proximal end of the lead into the distal end of the catheter and advancing the lead until the proximal lead end exits the proximal end of the catheter. The distal engaging member, which may be an electrode, is provided with a proximally facing, lateral surface that interacts with the distal end of the guide catheter to prevent the engaging member from entering the guide catheter.

The distal engaging member may be provided as a centric or acentric member extending from a distal electrode or the distal end of the lead body. The engaging member may be provided as a retractable member allowing the lead to be passed through the guide catheter from the proximal catheter end until the distal lead end exits the distal catheter end. Upon exiting the distal catheter end, the engaging member extends and engages with the distal catheter end.

The medical lead is characterized by a lead body having a high tensile strength such that traction applied to the proximal lead end is transferred in a substantially linear way to the distal engaging member. The lead body is preferably reinforced by a strengthening member, such as a polyester fiber, extending through the lead body lumen. The interaction of the lateral surface of the engaging member with the distal end of the guide catheter causes flexion of the distal, flexible catheter segment when traction is applied to the proximal lead end. This flexion results in a dynamic curvature of the distal catheter segment of varying radii, which variations are controlled by the amount of traction applied to the proximal lead end. The dynamic curvature of the distal segment allows the catheter to be precisely maneuvered through a range of geometries encountered in a vascular pathway.

In one method for using the guide catheter assembly and medical lead provided according to the present invention, the lead is first fed into the guide catheter, and the guide catheter is then advanced through a venous pathway. During advancement, tension may be maintained on the lead to hold the distal engaging member against the distal catheter end and prevent the engaging member from advancing ahead of the guide catheter. Traction is applied to the proximal lead end as necessary to deflect the distal segment of the catheter and thereby maneuver the guide catheter around obstacles or into desired venous branches. Visualization of the advancement of the guide catheter may be aided by fluoroscopy. Once the distal end of the catheter is located at a desired implant site, the lead may be fixed into position by wedging the engaging member in a narrow vessel lumen. The guide catheter may then be withdrawn over the lead body. A proximal lead extension may be provided over which the guide catheter may be withdrawn, leaving the lead implanted at the desired location.

The system provided by the present invention reduces the number of tools and steps required to guide a lead to an implant site, which, in turn, is expected to reduce the associated costs and procedural time for implanting a cardiac vein lead. Aspects of the present invention reduce the components required in a steerable guide catheter system allowing the overall catheter size to be reduced. The medical lead size may also be reduced since a guidewire or stylet is not needed, allowing the lead to be advanced deep into the cardiac veins for left heart sensing and/or stimulation.

BRIEF DESCRIPTION OF THE DRAWINGS

FIG. 5 is a side, cut-away view of the distal end of an alternative embodiment of a guide catheter and medical lead system.

FIG. 6 is an end view of the system of FIG. 5 showing an engaging member on the distal lead end interlocked with a notch at the distal catheter end.

FIG. 7A is a plan view of the guide catheter and medical lead system shown in FIG. 5.

FIG. 7B is a plan view of the guide catheter and medical lead system of FIG. 7A showing the distal guide catheter segment in a deflected position as it may be when traction is applied at the proximal lead end.

FIG. 8 is an alternative embodiment of a guide catheter and medical lead system wherein the distal engaging member is provided as an extension from the lead body rather than from a tip electrode.

FIG. 9 is a plan view of the guide catheter and medical lead system of FIG. 8 showing the engaging member in a retracted position to allow the lead to be passed through the guide catheter.

DETAILED DESCRIPTION OF THE INVENTION

Figure 1A:
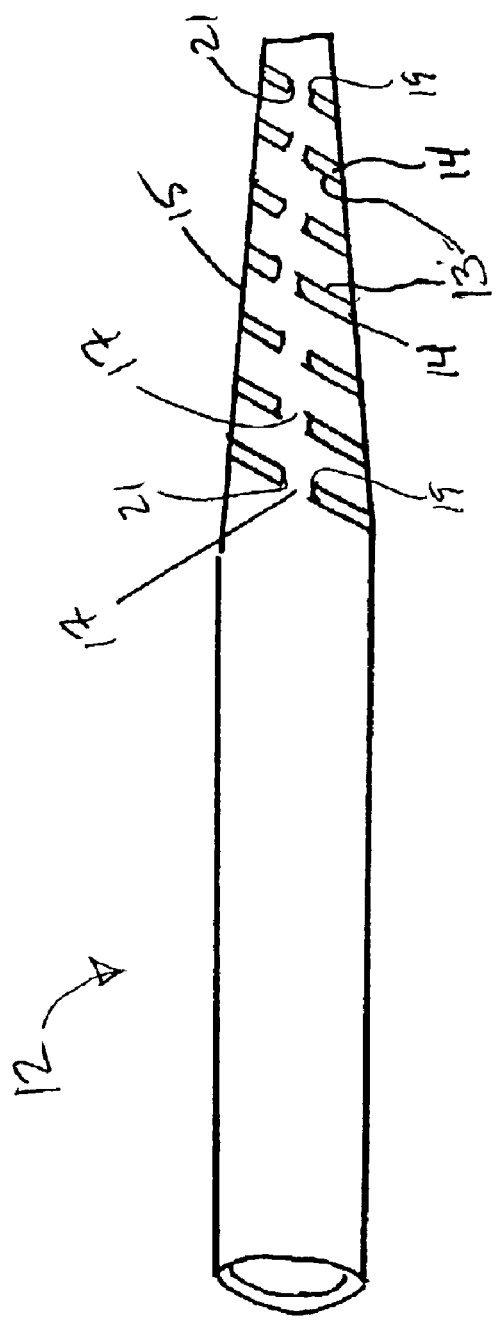
FIG. 1 is a plan view of a guide catheter and transvenous medical lead system in accordance with the present invention.

FIG. 1 is a plan view of a guide catheter and transvenous medical lead system in accordance with the present invention. As illustrated in FIG. 1, a guide catheter 8 according to the present invention includes a generally tubular catheter body 10 that is preferably formed from a biocompatible polymer such as polyurethane, a fluoropolymer, silicone rubber or other plastic acceptable for medical use. The catheter body 10 may optionally be reinforced with an embedded braiding or other reinforcing structure to provide stiffness to body 10 to allow advancement of catheter body 10 through a venous pathway. Catheter body 10, however, should also be flexible enough to adapt to a tortuous pathway. In one embodiment, catheter body 10 is preferably sized to allow passage through the coronary sinus to allow placement of a lead deep in the cardiac veins for left heart stimulation and/or sensing. As such, catheter body 10 preferably has an outer diameter on the order of approximately 4 to 5 French and an inner diameter sized to allow passage of a small diameter lead, for example on the order of approximately 2 French.

Catheter 8 includes a handle 6 located along a proximal segment 11 of catheter 8 for aiding in manipulating and advancing catheter 8 as catheter 8 is steered through a venous pathway to a target site. Catheter 8 extends from proximal segment 11 to a distal segment 12 that is characterized by having a greater flexibility than the remainder of catheter body 10. Distal segment 12 is preferably tapered and may be fabricated from a lower durometer plastic than the remainder of catheter body 10. The flexibility of distal segment 12 may be enhanced by being scored to form flexing structures 14 which may be provided as a spiral cut in the wall of the distal segment 12, corrugations, or other structures that would allow distal segment 12 to have greater flexing ability than the remainder of catheter body 10.

FIG. 1A is plan view of a distal segment of a guide catheter and transvenous medical lead system in accordance with the present invention. For example, as illustrated in FIG. 1A, flexing structures 14 of distal segment 12 are spiral cut to include individual cuts 13 so that each of the individual cuts 13 of flexing structure 14 extends approximately 140 degrees about the tapered portion 15 of distal segment 12 from a corresponding first end 19 to a second end 21. As a result, each of the individual cuts 13 includes a non-cut portion 27 of approximately 40 degrees extending about distal segment 12 between first end 19 to second end 21. Although each of individual cuts 13 are shown as being cut at the same 140 angle about distal segment 12, it is understood that the angle of cuts is not limited to 140 degrees, but rather, could be of any angle or combination of angles. According to a preferred embodiment of the present invention, individual cuts 13 are made at an angle corresponding to a pitch of a coil electrode 34 (FIG. 2) in order to maximize the resulting flexibility of distal segment 12.

A medical lead 20, which may be implanted with the aid of guide catheter 8, is preferably a small diameter lead, on the order of 2 French, such that lead 20 may be advanced into a cardiac vein to achieve left heart stimulation and/or sensing. In FIG. 1, lead 20 is shown exiting at proximal segment 11 of guide catheter 8. A connector assembly 24 at a proximal end 7 of lead 20 allows lead 20 to be connected to a medical device, such as a pacemaker or implantable cardioverter defibrillator, for example. Connector assembly 24 includes sealing rings 28, which will form a fluid tight seal with the inner surface of a medical device connector port, and a pin terminal 26 for providing electrical connection to the medical device.

Extending from pin terminal 26 is a lead extension 30. Lead extension 30 is provided to ease handling of lead 20 during an implant procedure. Specifically, extension 30 provides the additional length needed to remove guide catheter 8 over the lead 20 after lead 20 has been positioned at a desired implant location. Extension 30 may be a generally tubular construction formed from a polymer such as polyurethane. Extension 30 may be provided with a connection terminal 31 at a proximal end 33 of extension 31 that is electrically coupled via a conductor extending to pin terminal 26 through a center lumen of extension 30.

Figure 2:
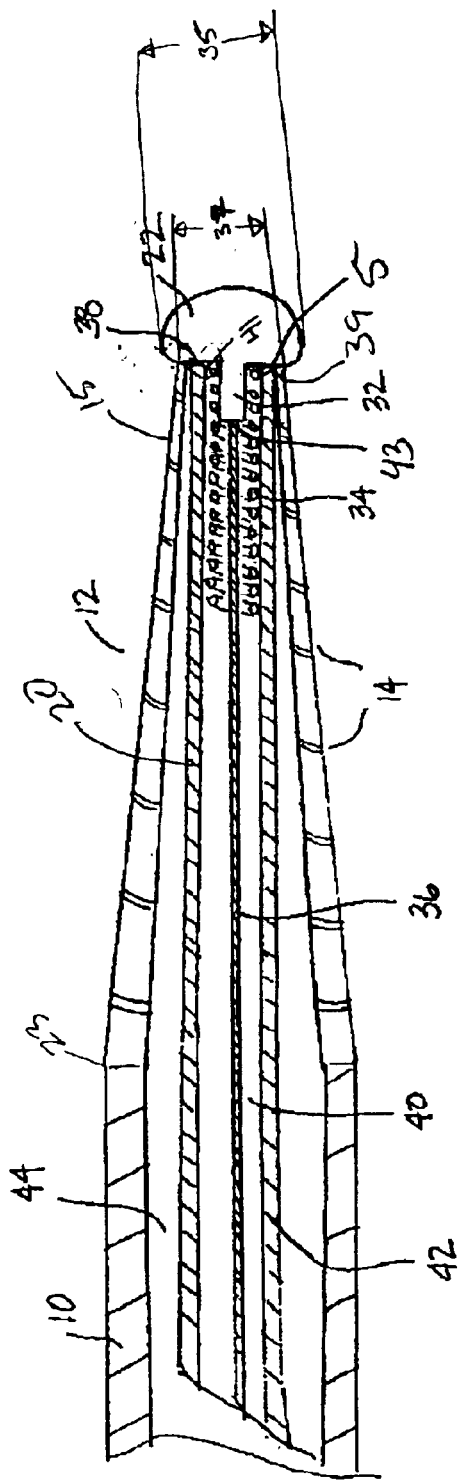
FIG. 2 is a side, cut-away view of the distal end of the lead and guide catheter shown in FIG. 1.

FIG. 2 is a side, cut-away view of a distal end of a lead and a catheter according to the present invention. As illustrated in FIG. 2, a distal end 5 of lead 20 includes an engaging member 22, inserted within catheter 8 at distal segment 12 of catheter 8. Engaging member 22 may have a generally hemispherical or "cup" shape and may be formed from a biocompatible, electrically conductive metal, such as platinum, iridium, or an alloy thereof, such that engaging member 22 may also function as an electrode. Tapered portion 15 of distal segment 12 gradually reduces in thickness as tapered portion 15 extends from a proximal end 23 of tapered portion 15 to a distal end 39 of segment 12, forming a slip fit with lead 20 as lead 20 is extended outward from catheter 8 at distal end 39 of segment 12. Engaging member 22 has an outer diameter 35 that is larger than an outer diameter 37 of catheter 8 at distal end 39 of segment 12. A proximal face 38 of member 22 engages against distal end 39 of flexible segment 12, forming a mechanical stop that prevents member 22 from entering catheter 8. Engaging member 22 may have a shape that is generally hemispherical, as shown, or may alternatively be generally wedge-shaped, ring-shaped, conical, spherical, or any other shape that provides an approximately laterally extending, proximally facing surface for engaging with the distal end of catheter 8.

Lead 20 is fed into a central lumen 44 of guide catheter 8 by passing lead extension 30 and lead 20 through an opening 41 at distal end 39 of guide catheter 8, and advancing the lead 20 from distal end 39 toward the proximal end 11 of catheter 8 until member 22 is engaged against distal end 39 of flexible segment 12 and the proximal end 7 of lead 20 exits a proximal opening of catheter 8.

Engaging member 22 is provided with an electrically conductive stem 32, which is electrically coupled, by welding, crimping or other appropriate coupling methods, to a conductor 34. Conductor 34 is preferably a coiled conductor but may also be a cabled or stranded conductor, which types of conductors are known in the art. Conductor 34 extends the length of lead body 42 through a lumen 40 and is further coupled to pin terminal 26 at the proximal lead end. Conductor 34 may optionally extend further through lead extension 30 to proximal connector 31 thereby providing an electrical pathway from connector 31 to engaging member 22. Electrical testing for verification that member 22 is at an acceptable implant site may be performed during an implant procedure by connecting a monitoring or stimulation device to connector 31.

In FIGS. 1 and 2, lead 20 is shown as a unipolar lead having a single electrode, provided as engaging member 22, and a single connector terminal 26. In other embodiments, lead 20 may be provided as a bipolar or multipolar lead having multiple connector terminals corresponding to any combination of ring electrodes, coil electrodes and/or other types of sensors in addition to the tip engaging member that may also serve as an electrode. In the embodiment shown in FIG. 2, engaging member 22 serves as an electrode as well as a mechanical stop to maintain the position of distal end 5 of lead 20 in approximate alignment with distal end of catheter 8 such that lead 20 may be used as a pull wire to steer catheter 8 during insertion of catheter 8 in the body, as will be described below. It is recognized that an engaging member may be provided at the tip of lead 20 that does not serve as an electrode. Thus engaging member 22 may be left uncoupled to any conductors and may be formed of a non-conductive, preferably rigid, biocompatible material.

Lead 20 is preferably reinforced by a tensile strengthening member 36. Tensile strengthening member 36 may take the form of a high-strength filament, such as a polyester fiber, extending the length of lead body 42 through lumen 40 and may be provided as generally disclosed in PCT Publication No. WO 01/80941 issued to Williams et al., incorporated herein by reference in its entirety. Tensile strengthening member 36 is fixedly attached at a distal end 43 to stem 32. Member 36 extends through pin terminal 26, provided as a hollow pin, and through a lumen of lead extension 30 such that member 36 is fixedly attached at a proximal end to the connector 31 of extension 30.

Hence, traction applied to lead extension 30 or proximal end 13 of lead 20 will be transferred to the engaging member 22 via strengthening member 36. When traction is applied at proximal end 7 of lead 20, force transferred from the proximal face 38 of engaging member 22 will cause flexible distal segment 12 of catheter 8 to bend in a flexed position, so that flexible distal section 12 is advanced from a non-flexed position (FIG. 2) to a flexed position (FIG. 3).

Figure 3:
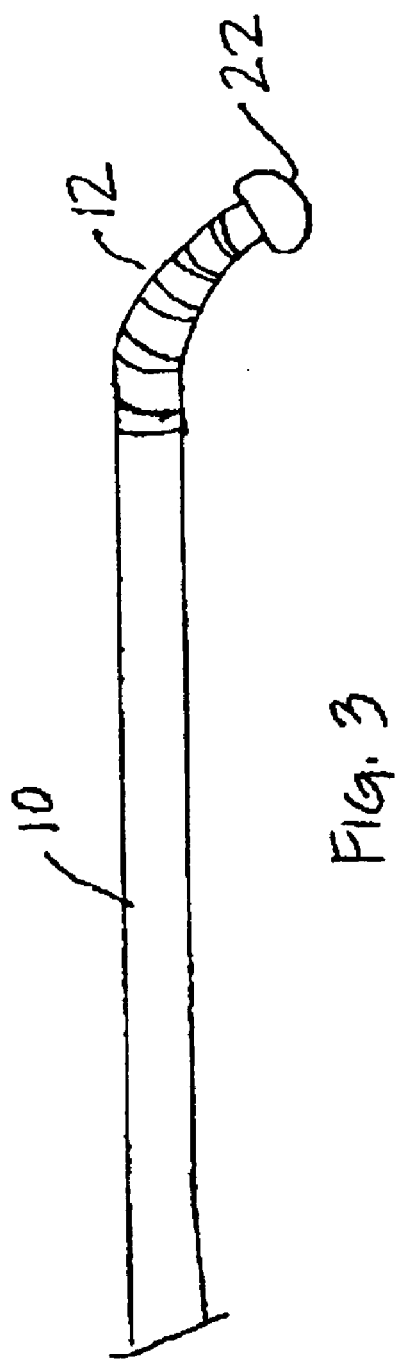
FIG. 3 is a plan view of the distal end of the catheter of FIG. 2 in a flexed position.

FIG. 3 is a plan view of a distal end of a catheter positioned in a flexed position using a transvenous medical lead system according to the present invention. As illustrated in FIG. 3, by applying traction to lead 20, the flexible distal segment 12 is deflected axially and radially in order to dynamically steer the catheter distal end in a desired direction to overcome an obstacle or direct the catheter 8 into a desired venous branch. The degree of curvature can be controlled by the amount of force or traction applied to the proximal lead end. In this way, when force is applied at proximal end 7 of lead 20, for example, force transferred from the proximal face 38 of engaging member 22 will cause flexible distal segment 12 of catheter 8 to bend in a flexed position, so that flexible distal section 12 is advanced from a non-flexed position (FIG. 2) to a flexed position (FIG. 3). According to the present invention, the degree of curvature can be controlled by the amount of force or traction applied to the proximal lead end, so that flexible distal segment 12 can be selectably positioned at any desired position between the flexed position and the non-flexed position.

Figure 3A:
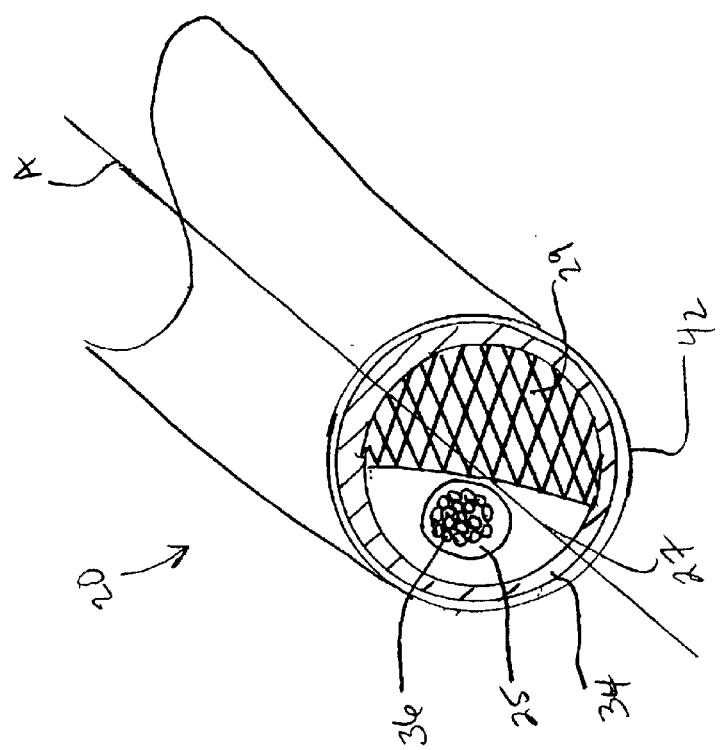

FIG. 3A is a cross-sectional view of a lead having a strengthening member according to an alternate embodiment of the present invention. In a preferred embodiment, strengthening member 36 extends through the center of central lumen 40 lead 20. However, in alternative embodiments, strengthening member 36 may be provided off-set from the central axis of lead 20 such that when traction is applied to the proximal end of lead 20, catheter distal segment 12 will be deflected in a predictable direction associated with the position of strengthening member 36. For example, as illustrated in FIG. 3A, according to an alternate embodiment of the present invention, strengthening member 36 is located within a member lumen 25 that extends through a conductor lumen 27, formed by conductor coil 34 of lead 20 and extending from proximal end 7 to distal end 5 of lead, so that member 36 extends through lead 20 in an offset positioned from a central axis A of lead 20. A fiber core 29 is positioned within lumen 27 outside of lumen 25 to aide in fixedly positioning lumen 25 within lumen 27.

Figure 4:
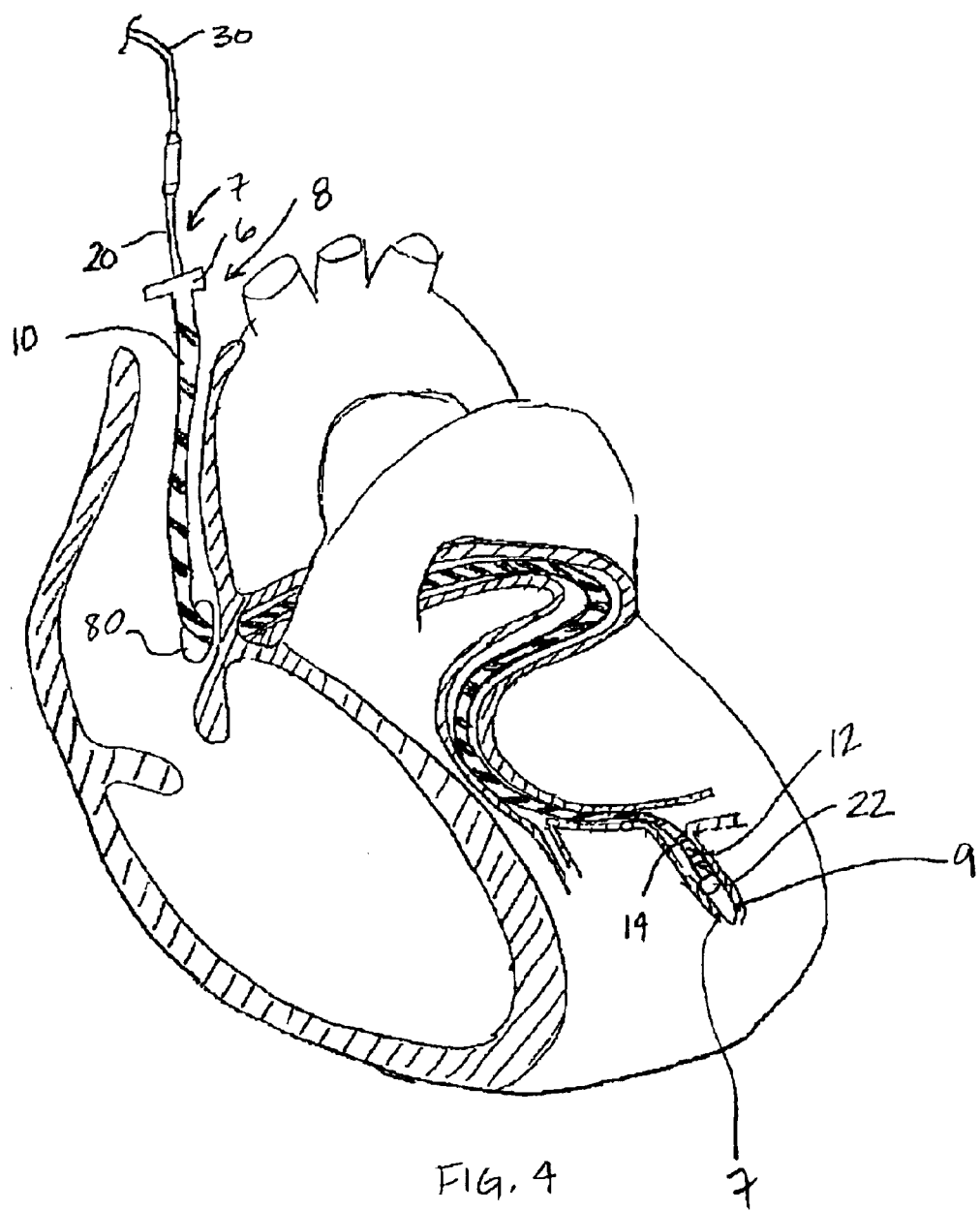
FIG. 4 is a partially cut-away view of a patient's heart in which the guide catheter and lead of FIG. 1 have been advanced through the coronary sinus ostium into the coronary sinus and further into a deep cardiac vein.

FIG. 4 is a partially cut-away view of a patient's heart in which the guide catheter 8 and lead 20 have been advanced through a coronary sinus ostium 80 into the coronary sinus and further into a deeper cardiac vein. During advancement, light tension is applied to proximal end 13 of lead 20 to maintain the position of engaging member 22 against distal end 39 of catheter 8 without flexing distal segment 12. Increased traction is then applied to lead 20 as needed to steer catheter 8 in a desired direction by flexing distal segment 12 as described above. Fluoroscopy may be used during the implant procedure to provide visualization of the catheter 8 position within the cardiovascular system. Once lead 22 is advanced deep into a cardiac vein, engaging member 22 will become wedged in a narrow lumen 9 of a blood vessel 7. The enlarged circumference of engaging member 22 at dashed line 46 (FIG. 2) enables member 22 to become wedged in vessel 7 and acts to improve electrical contact with the underlying epicardium of the heart when member 22 also serves as an electrode.

Once member 22 is properly positioned within vessel 7, catheter 8 is withdrawn by pulling catheter 8 over lead 20 and lead extension 30. The inner diameter of lumen 44 at distal end 39 of tapered distal segment 12 is sized to form a slip fit around lead body 42 such that catheter 8 may easily be withdrawn in a proximal direction over lead 20. In one embodiment, distal segment 12 may be provided with flexing structures 14, described above in reference to FIG. 1A, that form a helical spiral such that when catheter 8 is rotated in one direction relative to lead body 42, flexing structures 14 contract causing distal segment 12 to tighten down on lead body 42. When rotated in an opposite direction, flexing structures 14 expand causing distal segment 12 to loosen from lead body 42. Catheter 8 may be rotated in an appropriate direction during removal to ease the passage of catheter 8 over lead body 42.

FIG. 5 is a side, cut-away view of a distal end of an alternative embodiment of a guide catheter and medical lead system. As illustrated in FIG. 5, according to an alternate embodiment of the present invention, a distal end 105 of a lead 120 includes an engaging member 122 having a laterally extending flange 123 that abuts and is engaged against a catheter 108 at a slot 104 formed at a distal segment 112 of a catheter 108. According to the embodiment illustrated in FIG. 5, engaging member 122 is a tip electrode.

FIG. 6 is a perspective end view of the distal end of the guide catheter and medical lead system of FIG. 5. As illustrated in FIGS. 5 and 6, a distal end 139 of guide catheter 108 extends from a first end 111 to a second end 113. A slot 115 is formed at distal end 139 by a bottom wall 117, first end 111 and second end 113, in which flange 123 of engaging member 122 is received to engage engaging member 122 against distal end 139 of catheter 108 when lead 120 is inserted within catheter 108, as described above. Flange 123 of engaging member 122 extends outward from engaging member 122 along a radius generally defined by dashed line 118.

Guide catheter 108 and lead 120 are otherwise similar to catheter 8 and lead 20 described above, and have similar reference numerals. Therefore, description of those similar portions is omitted for brevity sake. However, as can be seen in FIG. 5, catheter 108 does not include tapered end 15, but rather has a straight end. It is understood, however, that catheter 108 could include a tapered end, as illustrated in catheter 8 above, and the present invention is intended to include either embodiment.

Similar to catheter 8 and lead 20 described above, engaging member 122, which may be an electrode, is provided with an electrically conductive stem 132 that is electrically coupled to a conductor 1134, shown as a coiled conductor. A strengthening member 136 extends through a center lumen 144 of conductor 134 to provide tensile strengthening to lead body 120 and to transfer traction applied at the proximal end 7 to strengthening member 122 as described previously.

FIG. 7A is a plan view of the guide catheter and medical lead system shown in FIG. 5 in a non-flexed position. As illustrated in FIG. 7A, flange 123 of engaging member 122 is fixedly positioned within slot 115 at distal end 139 of a flexible, distal segment 112 of guide catheter 108. Guide catheter 108 includes a handle 106 located along a proximal segment 111 of catheter 108 for aiding in manipulating and advancing catheter 108 as catheter 108 is steered through a venous pathway. Handle 106 is preferably oriented such that handle 106 extends along a radius that is parallel to the radius 118 along which flange 123 of engaging member 122 protrudes. Catheter 108 extends from proximal segment 111 to a distal segment 112 that is characterized by having a greater flexibility than the remainder of a catheter body 110. Distal segment 112 is preferably fabricated from a lower durometer plastic than the remainder of catheter body 110. The flexibility of distal segment 112 may be enhanced by including flexing structures 114 which may be provided as a spiral cut in the wall of the distal segment 112, corrugations, or other structures that would allow distal segment 112 to have greater flexing ability than the remainder of catheter body 110, as described above.

A proximal end of lead body 116 exits the proximal end of guide catheter 120 and terminates at a connector assembly 126. Connector assembly 126 may be provided with a pin terminal 128, corresponding to tip electrode 106. The lead may be provided with a lead extension 130, as described above in conjunction with FIG. 1.

FIG. 7B is a plan view of the guide catheter and medical lead system shown in FIG. 5 in a flexed position. As illustrated in FIG. 7A, once traction is applied to proximal end 107 of lead 120, the flexible distal segment 112 will deflect in a direction, indicated by arrow 144 and defined generally by radius 118, in a plane defined by a central axis 142 extending through catheter 108 and radius 118. Handle 106, in alignment with this radial direction of flexion, indicates the direction that segment 112 is deflected to a physician and the amount that segment 112 is advanced between the flexed position and the non-flexed position. The physician may rotate the catheter body 110 until handle 106 is pointed in a direction that distal segment 112 must be deflected in order to maneuver guide catheter 108 around an obstacle or into a desired blood vessel branch.

FIG. 8 is an alternative embodiment of a guide catheter and medical lead system in which a distal engaging member is provided as an extension from the lead body rather than a tip electrode. In FIGS. 5 through 7B, an acentric engaging member 104 was shown as a radial protrusion from tip electrode 122. An acentric or centric engaging member could also be provided as a radially protruding member from the lead body. For example, in FIG. 8 an engaging member is shown as a tine 204 extending from lead body 142. A generally hemispherical tip electrode 206 is provided with a conductive stem 208 that is electrically coupled to conductor 136. Conductor 136 is shown in this embodiment as a stranded or cabled conductor that is preferably provided with insulation 214 having a high Young's modulus. For example, insulation 214 may be provided as a high durometer polyurethane or polyimide as generally disclosed in U.S. Pat. No. 6,366,819 issued to Stokes, incorporated herein by reference in its entirety. Insulation 214 thus acts as a strengthening member for transferring traction applied at the proximal lead end to the distal lead end, to thereby cause flexion of distal segment 112 of catheter 108. Conductor 136 may alternatively be provided as a coiled conductor with a strengthening member provided as a fiber core through the lumen of the coil as described previously.

An engaging member may be provided such that it is retractable in order to allow the lead to be advanced through the guide catheter from the proximal catheter end. FIG. 9 is a plan view of the guide catheter and medical lead system of FIG. 8 showing an engaging member in a retracted position to allow a lead to be passed through a guide catheter. As illustrated in FIG. 9, tine 204 is preferably provided as a molded, plastic component which may pressed against lead body 210 to allow the lead to be passed through the lumen 144 of guide catheter 108. Once distal end 105 of lead 120 extends outward from distal end 139 of catheter 108, tine 204 will extend to its natural shape, as shown in FIG. 8. Tine 204 engages with distal end 139 of catheter 108 when tension is applied to proximal end 7 of lead 120, as described above.

A single tine 204 is shown in FIGS. 8 and 9, and may extend in a radial direction that is generally parallel to a catheter handle 106, as described above in conjunction with FIG. 7A. Tine 204 will cause flexion in a direction corresponding to the radial direction in which tine 204 extends, which may be indicated to a physician by the direction that the proximal handle is pointing. In other embodiments, two or more tines, or other types of generally radially-protruding, members having a proximally-facing, lateral surface may be provided on lead body 142 to act as engaging members with the distal catheter end.

Figure 10:
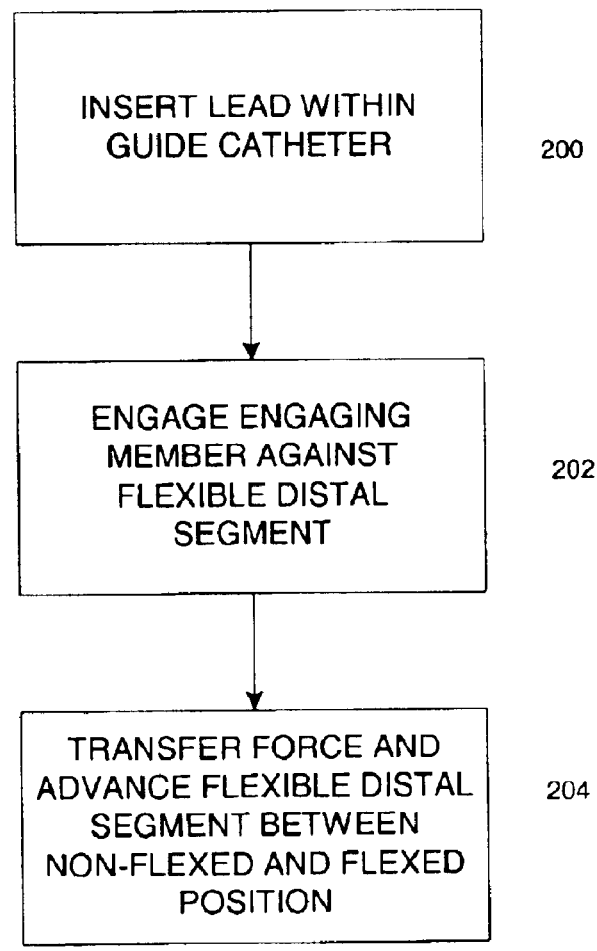
FIG. 10 is a flowchart of a method for advancing a medical electrical lead to a target site, according to the present invention.

FIG. 10 is a flowchart of a method for advancing a medical electrical lead to a target site, according to the present invention. As illustrated in FIG. 10, according to the present invention, a lead is first inserted within a guide catheter, Step 200, so that an engaging member, described above, of the lead is engaged against the flexible distal section of the guide catheter, Step 202, and the guide catheter is then advanced through a venous pathway to the target site. During advancement, tension may be maintained on the proximal end of lead that is transferred to the engaging member to hold the distal engaging member against the distal catheter end and prevent the engaging member from advancing ahead of the guide catheter. Traction is applied to the proximal lead end as necessary to deflect the distal segment of the catheter through the engaging member of the lead, and advance the flexible distal segment between the non-flexed position and the flexed position, Step 204, as described above, and thereby maneuver the guide catheter around obstacles or into desired venous branches. Visualization of the advancement of the guide catheter may be aided by fluoroscopy. Once the distal end of the catheter is located at a desired implant site, the lead may be fixed into position by wedging the engaging member in a narrow vessel lumen. The guide catheter may then be withdrawn over the lead body.

Thus a guide catheter and medical lead system provided by the present invention allows a guide catheter and lead to be steered to a desired implant site without requiring additional guidewires or stylets, or additional steering components such as pull wires incorporated in the guide catheter. A reduction in the number of steps and the number of instruments required for placing the medical lead is expected to reduce the procedure time and cost. The embodiments described herein have generally referred to a cardiac vein lead and guide catheter, however, the inventive system could be adapted for other types of cardiac leads, other types of leads, or other medical instruments requiring placement in a body vessel or organ. The description provided herein should therefore by considered exemplary and not limiting in regard to the following claims.

I claim:

1. A medical electrical lead system, comprising:
   a catheter extending from a proximal segment to a flexible distal segment, the distal segment having a first distal end;
   a lead, insertable within the catheter, extending from a proximal end to a second distal end;
   an engaging member positioned along the second distal end and engaged against the first distal end when the lead is inserted within the catheter, the engaging member transferring force exerted at the proximal end of the lead to the flexible distal segment and advancing the flexible distal segment from a first position to a second position, wherein the flexible distal segment is scored to form a plurality of cut portions, each of the plurality of cut portions extending about the flexible distal segment from a first end to a second end and including a non-cut portion positioned between the first end and the second end.

2. The system of claim 1, wherein each of the plurality of cut portions extends approximately 140 degrees about the flexible distal segment from the first end to the second end, and the non-cut portion extends approximately 40 degrees from the second to the first end.

3. The system of claim 1, further comprising a coiled conductor extending within the lead and coupled to the engaging member, the coiled conductor having a plurality of coils having a predetermined pitch, wherein the plurality of cut portions correspond to the predetermined pitch.

4. A medical electrical lead system, comprising:
- a catheter extending from a proximal segment to a flexible distal segment, the distal segment having a first distal end;
- a lead, insertable within the catheter, extending from a proximal end to a second distal end;
- an engaging member positioned along the second distal end and engaged against the first distal end when the lead is inserted within the catheter, the engaging member transferring force exerted at the proximal end of the lead to the flexible distal segment and advancing the flexible distal segment from a first position to a second position, further comprising a strengthening member, fixedly attached to the engaging member, transferring the force exerted at the proximal end of the lead to the engaging member.

5. The system of claim 4, wherein the strengthening member extends along a central axis of the lead.

6. The system of claim 4, wherein the strengthening member extends in an off-set position relative to a central axis of the lead.

7. The system of claim 4, wherein the strengthening member is a polyester fiber.

\* \* \* \* \*